United States Patent [19]

Forssmann et al.

[11] Patent Number: 5,744,444
[45] Date of Patent: Apr. 28, 1998

[54] HPTH-FRAGMENT-(1-37), THE PREPARATION THEREOF, MEDICAMENTS CONTAINING SAME AND THE USE THEREOF

[75] Inventors: Wolf-Georg Forssmann, Hanover; Franz Herbst, Nussloch; Peter Schulz-Knappe, Neustadt; Knut Adermann, Hanover; Michael Gagelmann, Schriersheim, all of Germany

[73] Assignee: HaemoPep Pharma GmbH, Hanover, Germany

[21] Appl. No.: 440,117

[22] Filed: May 12, 1995

Related U.S. Application Data

[63] Continuation of Ser. No. 155,658, Nov. 22, 1993, abandoned, which is a continuation of Ser. No. 863,291, Jun. 29, 1992, abandoned.

[30] Foreign Application Priority Data

Oct. 27, 1989 [DE] Germany .................. 39 35 738.4
Oct. 25, 1990 [WO] WIPO .................. PCT/EP90/01807

[51] Int. Cl.$^6$ .................. A61K 38/17; C07K 4/435
[52] U.S. Cl. .................. 514/12; 530/324; 530/412; 435/69.1; 514/2
[58] Field of Search .................. 530/300, 324, 530/412; 435/69.1; 514/2, 12

[56] References Cited

FOREIGN PATENT DOCUMENTS 0293159  11/1988  European Pat. Off. .

OTHER PUBLICATIONS

Sung et al., Biochemistry and Cell Biology, v. 64, p. 133 1986.
Niall et al., PNAS, v. 71, p. 384, 1974.
Kruse et al., 1986, Acta Endocrinologica, 30, 193, #221.
Hesch et al., 1984, Horm. Metabol. Res., 16, 559–560.
Jacobs et al., 1985, Nature, 313, 806–810.
S. Sakakibara, "Human Parathyroid Hormone Peptide Fragment", Patent Abstracts of Japan, vol. 7, No. 39, (C-151) (1184).
J.E. Zull et al., "Characterization of Parathyroid Horome Fragments Produced by Cathepsin D", Chem. Abs., vol. 102, No. 17, Apr. 29, 1985, & J. Biol. Chem., vol. 260, No. 3, pp. 1608–1613, 1985.
S. Pillai et al., "Production of Biologically Active Fragments of Parathyroid Hormone by . . .", Chem. Abs., vol. 106, No. 5, Feb. 2, 1987, J. Biol. Chem., vol. 261, No. 32, pp. 14919–14923, 1986.

Primary Examiner—Stephen Walsh
Assistant Examiner—Sally P. Teng
Attorney, Agent, or Firm—Nikaido, Marmelstein, Murray & Oram LLP

[57] ABSTRACT

The invention relates to a peptide from human blood, designated as hPTH-(1-37), the structure of which was elucidated for the purpose of the diagnostic, medical and commercial utilization thereof. The isolation of a fragment hPTH-(38-84) proves the existence of the hPTH-(1-37). A removal of amino-terminal amino acids from the hPTH fragment-(1-37) reduces its biological activity. The hPTH-(1-37) circulating in the blood is identical with the synthetic reference substance hPTH-(1-37), however not with fragments such as hPTH-(1-33), hPTH-(1-34) or hPTH-(1-38). The molecule form hPTH-(1-37) has been proven by mass spectrometry (plasma desorption method). A different biological activity and differences in the three-dimensional peptide structure of the hPTH fragment-(1-37) in comparison to other hPTH fragments furnish evidence of that this fragment is the preferential natural peptide of the parathormone family which should be used for the treatment of diseases of the parathyroid, circulatory system, respiratory system, male genital organ and kidneys.

6 Claims, 17 Drawing Sheets

HPTH-FRAGMENT-(1-37), THE PREPARATION THEREOF, MEDICAMENTS CONTAINING SAME AND THE USE THEREOF

This application is a continuation of application Ser. No. 08/155,658, filed Nov. 22, 1993, now abandoned, which is a continuation of Ser. No. 07/863,291, filed Jun. 29, 1992, now abandoned.

The present invention relates to a hPTH fragment-(1-37), to the preparation thereof, to medicaments containing said fragment and to the use thereof.

Human parathormone (hPTH), the hormone of the parathyroids, is a potentially important therapeutic aid, e.g. for the treatment of osteoporosis and of hypopara thyroidism.

Osteoporosis (reduction in bone mass) (Riggs and Melton, N. Engl. J. Med. 314, 1676–1686, 1986) is a frequently occurring disease which mainly afflicts women in the menopause and elderly people. The persons affected suffer from, depending on the intensity, frequent fractures in the region of the backbone, the forearm or thigh, pain up to complete immobility, loss of fitness for work and of social contacts and a higher mortality risk. For the time being, healing is considered to be hardly possible (Consensus Development Conference: Prophylaxis and Treatment of Osteoporosis, 1987). Experimental studies with animals (Selye, Endocrinology 16, 547–558, 1932; Kalu et al., Lancet 1363–1366, 1970; Hefti et al., Clin. Science 62, 389–396, 1982; Tam et al., Endocrinology 110, 506–512, 1982; Podbesek et al., Endocrinology _1 _1 _2, 1000–1006, 1983; Gunness-Hey and Hock, Metab. Bone Dis. & Rel. Res. 5, 177–181, 1964) as well as more recent histological findings upon primary hyperparathyroidism (Delling et al., Klin. Wochenschr. 65, 643–653, 1987) suggest that an increase in the bone mass may be accomplished by a treatment with PTH. Reeve et al. (Br. Med. J. 1340–1344, 1980) indeed achieved an improvement in the trabecular bone structure of patients suffering from osteoporosis by daily administration of small doses of PTH, however with a concomitant slight decrease in cortical bone mass. Recent findings suggest that PTH, with a simultaneous administration of bone-active substances such as, e.g., 1,25-vitamin-D3 (Slovik et al., J. Bone Miner. Res. 1, 377–381, 1986), calcitonin (Hesch et al., Calcif. Tissue Int. _4 _4, 176–180, 1989) or estrogen (Reeve et al., Proceedings of the 5th International Congress on Bone Morphometry, Niigata, Jul. 24–29, 1988) increases the bone mass of the Spongiosa without Corticalis loss.

Hypoparathyroidism (PTH deficiency) (Kruse, Monatsschr. Kinderheilkunde 136, 652–666, 1988) occur either congenitally or as a consequence of surgery or of radiation treatment in the cervical region and results in a decreased calcium concentration in blood. The patients tend to have convulsive fits. If the PTH deficiency does already exist during childhood, a reduced mental development and a defective tooth and bone development are threatened. While a therapy with calcium and/or vitamin D preparations will in most patients normalize the calcium concentration in serum, it goes along with an increased risk of kidney damage. This risk of a medicament treatment can be avoided by a hormone substitution therapy with PTH.

Finally, it has most recently been shown that the parathyroid hormone exhibits a blood pressure lowering activity (Nickols, Blood Vessels, 24, 120–124, 1987).

In the treatment of osteoporosis and hypertonia as well as in the hormone substitution in the case of hypoparathyroidism, the PTH must be regularly administered over an extended period of time, if necessary lifelong. Therefore, the PTH administered must be free from impurities and must not induce the formation of antibodies. This requirement can be most efficiently met by peptides with the amino acid sequence of human PTH which have been synthesized via the chemical route or by genetic engineering. The secreted PTH molecule consists of 84 amino acids [hPTH-(1-84)]. However, peptides of this order of magnitude are difficult to synthesize chemically and may be more easily prepared by genetic engineering.

Hitherto, two different peptides having the amino-terminal partial sequences of the human PTH—the hPTH-(1-34) and the hPTH-(1-38)—have been synthesized. In the clinical tests under the regimen of one single injection for a diagnostic application, the short-term effects expected from previous experience with extracted bovine PTH (bPTH) were observed with hPTH-(1-34) (Mallette et al., J. Clin. Endocrin. Metab. 67, 964–972, 1988) as well as with hPTH-(1-38) (Kruse and Kracht, Eur. J. Pediatr. 146, 373–377, 1987), i.e. the temporary stimulation of the excretion of phosphate and cyclic adenosine monophosphate (cAMP) in the urine and a temporary increase of the cAMP concentration in the plasma.

In the therapeutical test of said peptides with a small number of osteoporosis patients, with hPTH-(1-34) (Reeve et al., Proceedings of the 5th International Congress on Bone Morphometry, Niigata, Jul. 24–29, 1988) as well as with hPTH-(1-38) (Hesch et al., Calcif. Tissue Int. 44, 176–180, 1989) some success could be achieved.

The disadvantage of the PTH fragments so far available, however, is that in some patients they provoke the formation of antibodies which may reverse the effect provided by the exogenously supplied fragments or even of the endogenous PTH [cf., for example, for hPTH-(1-34) Audran et al., J. Clin. Endocrin. Metab. 64, 937–943, 1987, and for hPTH-(1-38) Stögmann et al., Monatsschr. Kinderheilk. 136, 107, 1988.]

About twenty years ago, Berson and Yalow (J. Clin. Endocrinol. Metab. 28, 1037–1047, 1968) demonstrated that various PTH fragments occur in human plasma which could have been formed either by a fast peripheral degradation of the total molecule or by secretion of PTH fragments. It was shown that the products, the amounts of which prevailed in the circulation, of the peripheral pTH metabolism are large carboxy-terminal fragments having no biological activity which are formed in the liver (cf., for example, D'Amour and Huet, Am. J. Physiol. 246, E249–255, 1984). On the basis of the experimental results available it was assumed that with an intact renal function the hPTH-(1-84) is the dominant biologically active PTH form. In contrast, with a restricted renal function, there appeared a clearly visible peak in the elution position of the hPTH-(1-34) in fractionated plasma of the respective patients (cf. Grunbaum et al., Am. J. Physiol. 247, E442–448, 1984).

The existence of a biologically active PTH fragment circulating in human plasma of healthy patients could so far not be detected.

Therefore, various attempts have been made to simulate the endogenous decomposition of the PTH by in vitro investigations, thereby to draw conclusions with respect to primary cleavage positions in the total molecule. In this context, nearly each of the positions between the amino acids No. 5 and No. 43 of the amino-terminal end of the chain has been contemplated (cf., for example, Barling et al., Int. J. Biochem. 16, 815–821, 1984). Zull and Chuang (J. Biol. Chem. 260, 1608–1613, 1985), among others, carried out investigations with bPTH and cathepsin D. They were able to prove that upon the enzymatic decomposition of bovine PTH (bPTH) with the enzyme derived from bovine spleen the C-terminal fragments (35-84) and (38-84) and the complementary N-terminal fragments (1-34) and (1-37) are formed. The bPTH described in that paper is distinguished from the fragment hPTH-(1-37) found by us in the positions 1 (Ser instead of Ala), 7 (Leu instead of Phe), and 16 (Asn instead of Ser). The last-mentioned bovine fragments proved to be biologically active in in vitro investigations with kidney membranes of rat and bovine origin, while, however, the fragment-(1-37) was detectable only in very low amounts and was rapidly hydrolyzed to form the fragment-(1-34). The authors concluded therefrom that the final product of the enzymatic decomposition with cathepsin D of PTH in the bovine is the fragment-(1-34). In contrast thereto, other authors doubted that in vivo any N-terminal fragments would occur at all in the plasma (cf., for example, Goltzmann et al., J. Clin. Invest. 65, 1309-1317, 1980). Thus, no biologically active N-terminal PTH fragments formed by a peripheral degradation could be identified in normal rats (Bringhurst et al., Am. J. Physiol. 255, E886-893, 1982). MacGregor et al., (J. Biol. Chem. 261, 1929-1934, 1986) found that bovine parathyroids in culture do not secrete any biological active N-terminal PTH fragments. In summary, these findings at the date of the present invention suggested that no biologically active N-terminal PTH fragments circulate in human or animal blood plasma.

It is the object of the present invention to provide a new hPTH fragment-(1-37) which is a well accessible medicament having the biological and therapeutic activity of natural parathormone (PTH), which at least has the effectiveness of the known hPTH fragments (1-34) and (1-38) and avoids their drawbacks inherent thereto—and especially the induction of the antibody formation.

It is a further object of the present invention to provide a preparation method for this hPTH fragment-(1-37) and the use thereof as medicament for various therapeutic and diagnostic indications.

These objects are attained by a hPTH fragment with a novel amino acid sequence.

Thus, the present invention relates to a hPTH fragment-(1-37) having the amino acid sequence SEQ ID NO:1

Ser-Val-Ser-Glu-Ile-Gln-Leu-Met-His-Asn-Leu-Gly-Lys-His-Leu-Asn-
Ser-Met-Glu-Arg-Val-Glu-Trp-Leu-Arg-Lys-Lys-Leu-Gln-Asp-Val-His-
Asn-Phe-Val-Ala-Leu and its natural and pharmacologically compatible derivatives, especially amidated, acetylated, phosphorylated and glycosylated hPTH-(1-37) derivatives.

The present invention further relates to a method for preparing this hPTH fragment-(1-37) or the derivatives thereof, said method being characterized in that said fragment is prepared via a prokaryotic or an eukaryotic expression and is purified by means of chromatography, and to a further method for preparing the hPTH fragment-(1-37) or the derivatives thereof by isolating said fragment from human blood by chromatographic procedures in a known manner, and finally to a method for preparing the hPTH fragment-(1-37) or the derivatives thereof by preparing said hPTH fragment by the conventional methods of solid phase and liquid phase synthesis from the protected amino acids contained in the sequence as set forth, deblocking it and purifying it by means of the established chromatographic procedures.

According to the invention it has surprisingly been found that the shortest hPTH fragment exhibiting full biological activity, which is formed by the primary cleavage of the hPTH-(1-84) in the human body, is the hPTH-(1-37) (cf. Example 1). It has also surprisingly been found that the spatial structure of hPTH-(1-37) is clearly distinguished from those of the fragments hitherto known (cf. Example 5), which fact points to its specific structure-effect relations and antigen properties.

The hPTH fragment-(1-37) has been chemically synthesized (cf. Example 2) and has been formulated as a medicament. Also the preparation by genetic engineering using conventional vectors has been elaborated: Via the genetic engineering route the hPTH-(1-37) peptide is prepared (1) in prokaryotic organisms as well as (2) in eukaryotic organisms. For the prokaryotic expression, we prefer to utilize *Escherichia coli*. Available for this purpose are, among others, expression vectors for the secretory expression (e.g. pSP6, pRit-derivatives, Pharmacia), for the direct cytoplasmic expression (e.g. pKK-derivatives, Pharmacia) or expression as fusion protein (pMC1871, Pharmacia) (literature see in Marston et al., Biochem. J. 240, 1-12, 1986). For the eukaryotic expression we are able to make use of various organisms and vectors, e.g. insect cells (Summers and Smith, Tex. Agric. Exp. Stn. (bull) 1555, 1987), yeasts (Hitzemann et al., Nature 293, 717-722, 1981), filamentous fungi (Yelton et al., Proc. Natl. Acad. Sci. USA, 81, 1470-1474, 1984) and mammal cells (Zettlmeissl et al., Biotechnology 5, 720-725, 1987), among which we prefer to use the insect cells. The expressed peptide is purified by methods of chromatography, preferably as set forth in Example 1.

The medicament formulation contains hPTH-(1-37) or a physiologically compatible salt of hPTH-(1-37). The form and composition of the medicament containing the hPTH-(1-37) depends on the kind of administration. Human hPTH-(1-37) may be administered parenterally, intranasally, orally and by way of an inhalation. It is preferred to formulate hPTH-(1-37) into a preparation for injection, either as a solution or as a lyophilizate to be dissolved immediately before use. The medicament formulation may further contain auxiliary materials which are desired or necessary to meet the requirements of dispensing, to contribute to the solubility, stability or sterility of the medicament or to increase the efficiency of the absorption in the body. The daily dose to be administered depends on the indication. In the therapy of osteoporosis by i.v./i.m. injection, the daily dose is within the range of from 100 to 1,200 units (µg)/day, while for a daily subcutaneous injection it is preferably 300 to 2,400 units (µg)/day. The determination of the biological activity is based on measurements against international reference preparations and reference preparations by our laboratory for human PTH fragments in a common biological assay for hPTH fragments.

The fragment according to the invention hPTH-(1-37) is particularly suitable as a long-term therapeutic for hypoparathyroidism and osteoporosis, because it exhibits an excellent biological activity and, on the other hand, does not induce any immunoreaction even in the case of a life-long treatment.

The preparation according to the invention is further suitable as a blood pressure-stabilizing agent for a long-term or permanent treatment of essential hypertonia.

The preparation according to the invention is further to be applied as an agent for the therapy of renal diseases, in the intensive care, and for the therapy of lung diseases (cf. Example 6).

The preparation according to the invention is further to be employed as an agent for the therapy of male impotence (cf. Example 6).

The invention is further illustrated by means of Examples and of the Figures to which reference is made in the Examples.

The IBMX control values without PTH fragments were 18.0, 26.1, 20.9. The values depicted are average values S.D.

Figure 13:
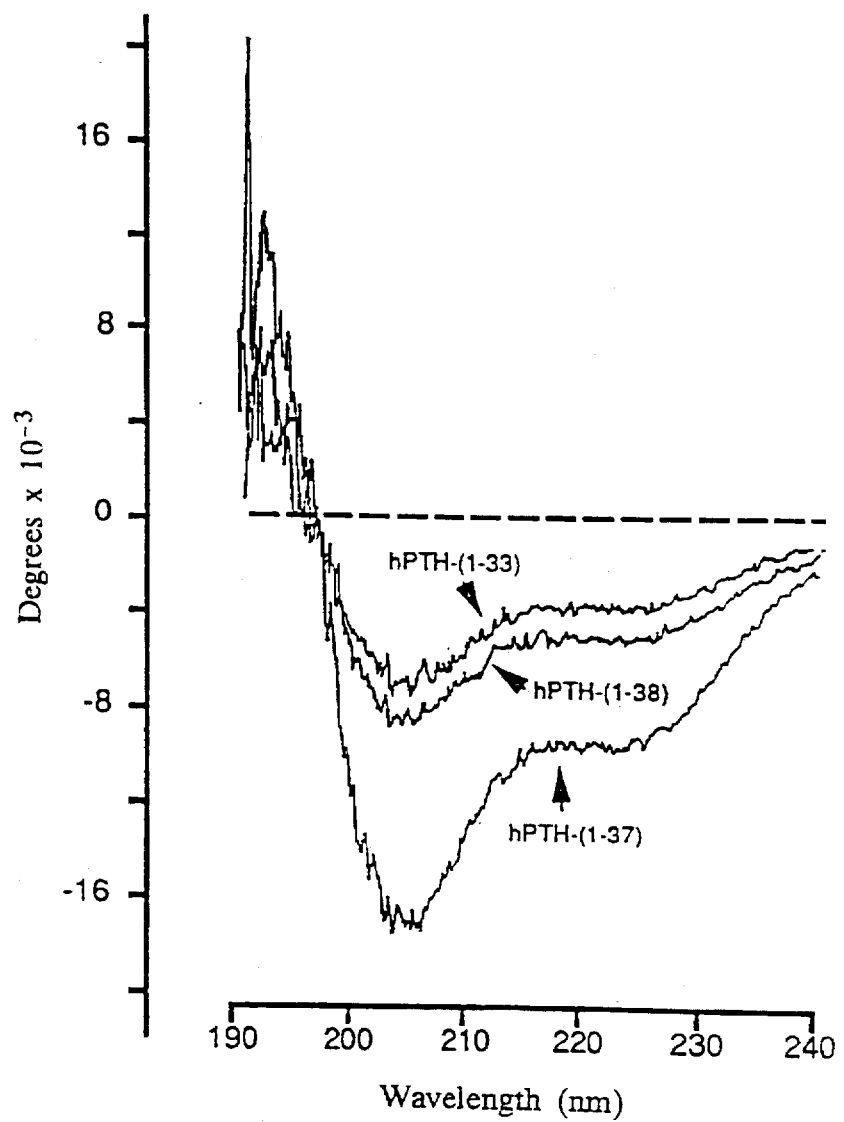

FIG. 13: UV circular dichroism spectra of the PTH fragments hPTH-(1-33), hPTH-(1-37), and hPTH-(1-38). In comparison to other hPTH fragments, the hPTH-(1-37) has a particularly prominent structure.

Figure 14:
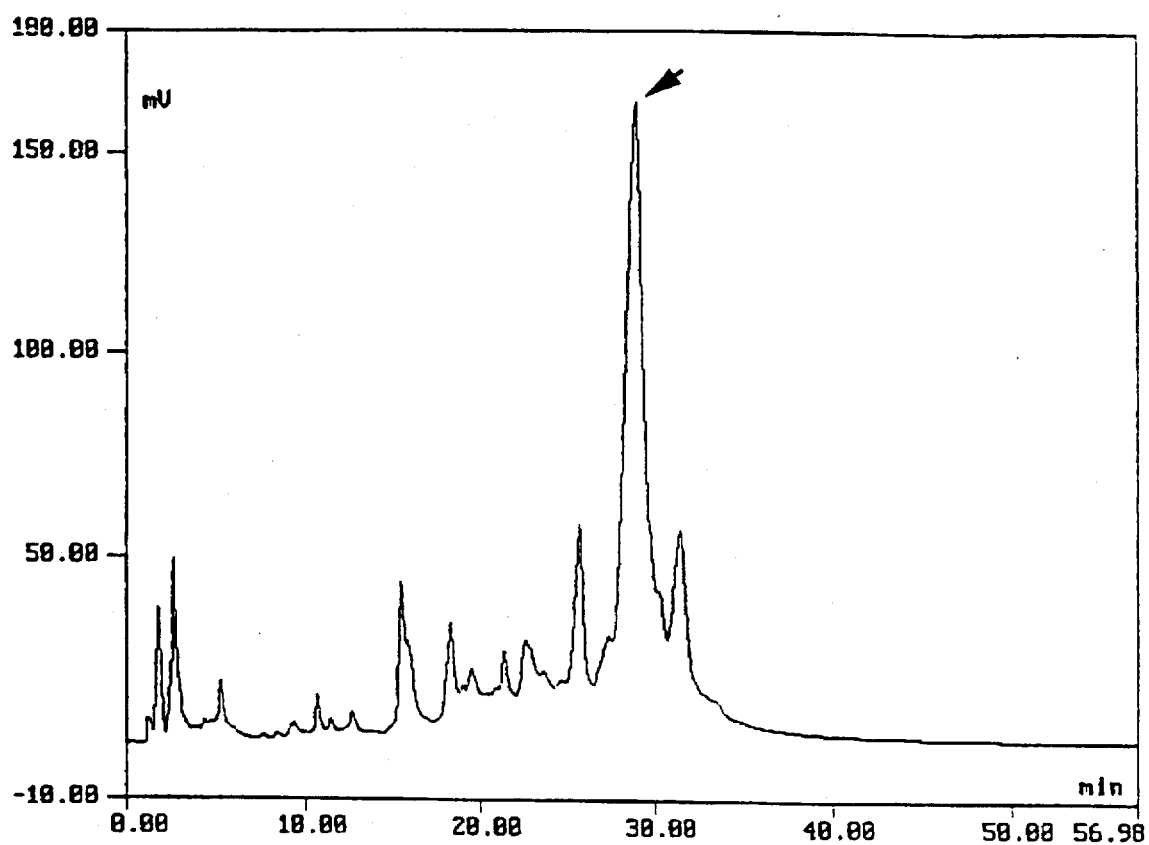
Figure 15:
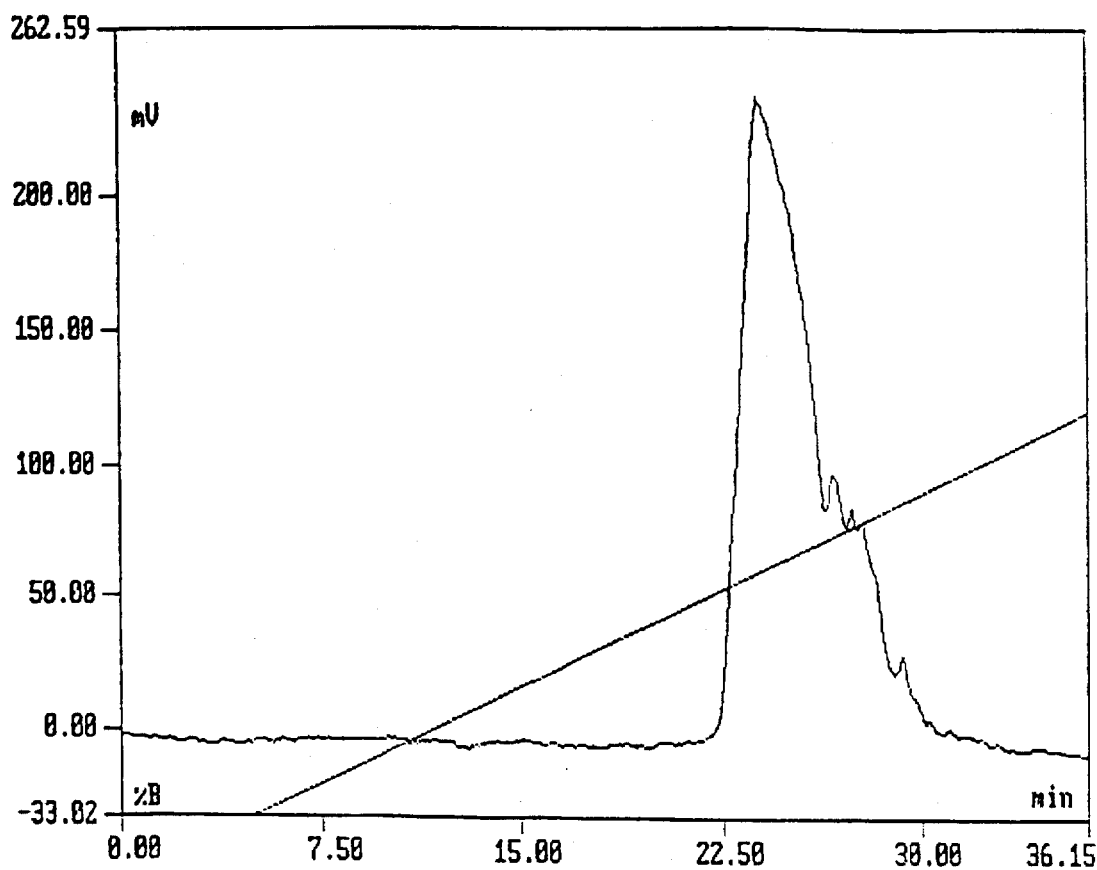

FIG. 14: Purification of the chemically synthesized hPTH-(1-37) in the first step. Here, a cation exchanger chromatography was carried out for the crude product. According to the reference, the synthetic hPTH-(1-37) appears in the higher peak at a retention time of 29 min (arrow).
Column: Parcosil PepKat 300-7, 125×4 mm
Temperature: 25° C.
Eluant: A: 5 mM NaH2PO4
B: 5 mM NaH2PO4, 1M NaCl, pH=3.0
Gradient: Start:—5% B 57 min—100% B
Absorption: 230 nm
Flow Rate: 1 ml/min FIG. 15: Reversed-phase HPLC chromatography of the pre-purified material of FIG. 14 on a semi-preparative scale. A main peak eluting from 22.50 min is obtained which corresponds to the reference of hPTH-(1-37).
Column: Parcosil ProRP 300-7, C4, 100×20 mm
Temperature: 25° C.
Absorption: 230 nm
Eluant: A: 0.1% trifluoroacetic acid
B: like A+80% acetontrile
Gradient: 0–100% B in 60 min
Flow Rate: 7 ml/min FIG. 16: Reversed-phase HPLC chromatography of the material of FIG. 15 with the representation of the final purification. The peak corresponds to the reference of chemically synthesized hPTH-(1-37).
Column: Parcosil ProRP 300-18, C4, 125×4 mm
Temperature: 25° C.
Absorption: 230 nm
Eluant: A: 0.1% trifluoroacetic acid
B: like A+80% acetontrile
Gradient: 0–100% in 60 min
Flow Rate: 0.7 ml/min FIG. 17: Plasma desorption mass spectrum of the synthetic hPTH-(1-37) from the preparation of FIG. 16. The molecular weight found of MW 4398.1 is identical with the theoretically calculated mass of MW 4401.0 of the molecule within an error range of <0.1%. Side sequences are not visible. The peak at MW 2201.5 corresponds to the double-ionized form, also within the limits of error of the measurement. This mass determination was confirmed by counter-sequencing.

EXAMPLE 1

Indirect Determination of the Sequence of a Circulating, Biologically Active PTH Fragment The starting material employed was a hemofiltrate which is obtained in large amount upon the treatment of patients suffering from renal insufficiency and contains all plasma constituents up to a molecular size of about 20,000 Dalton.

I. Recovery of the crude peptide material

The hemofiltrate was recovered by means of a hemofiltration apparatus from the company Sartorius using cellulose triacetate filters having an exclusion size of 20,000 Dalton (Type SM 40042, Sartorius, Göttingen, Germany). The filtrate was derived from renal insufficiency patients who were in a stable metabolism condition due long-term hemofiltration. 1000 liters of hemofiltrate were recovered and immediately after the recovery protected against proteolytic decomposition by flow-heating, acidifying and addition of enzyme inhibitors. Then a crude peptide fraction (about 100 g) was isolated by extraction with alginic acid according to the method of Forssmann disclosed in the DE 36 33 797 A1.

II. Isolation of a fraction (Code 51.5) exhibiting immunoreactivity in medium-regional- and C-terminal-specific radio-immunoassays for parathormone (PTH)

1. De-salting the crude peptide material using Sephadex G-25

Figure 1:
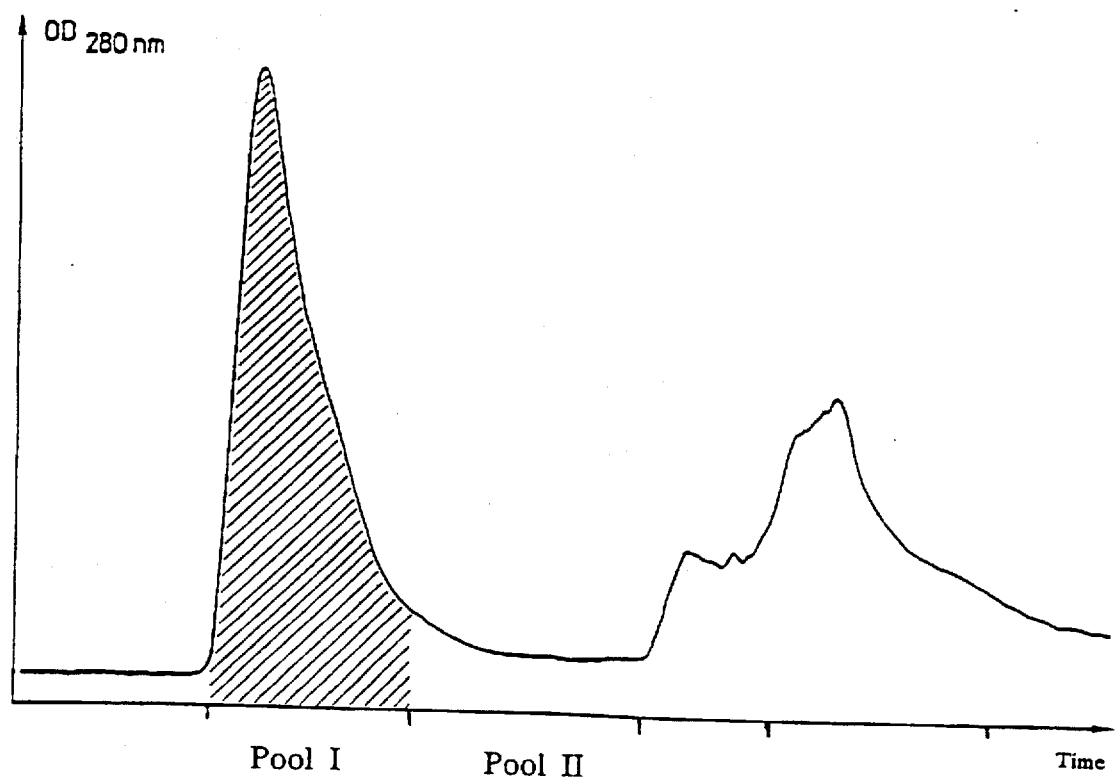
FIG. 1: Sephadex G 25—Preparative large-scale gel chromatography of the alginic acid eluates for a rough separation by molecular weights and for de-salting the crude peptide extract. The hPTH fragments determined by RIA are found in the hatched area.
Column: Pharmacia K 100/100; ID 10 cm×80 cm
Material: Sephadex G 25 medium
Eluant: 1M Acetic acid
Flow Rate: 5 ml/min
Absorption: 280 nm

The crude peptide fraction obtained from the alginic acid extraction was subjected to a gel-chromatic separation at 8° C. on a column filled with Sephadex G-25 (Pharmacia, Uppsala, Sweden) equilibrated with 1M acetic acid (FIG. 1).

The immunoreactivity in the Pools I through IV was measured in a radioimmunoassay (RIA) for human PTH with medium-regional specificity [hPTH-(44-68)-RIA, company Immundiagnostik, Darmstadt, Germany]. According to the data provided by the producer, the lower limit of detection is 6 fmoles/test of the standard employed [hPTH-(44-68)]. Intra-Assay and inter-Assay variation coefficients are from 10 to 13% and from 12 to 21%, respectively. The synthetic hPTH peptides hPTH-(1-34), hPTH-(28-48) and hPTH-(64-84) do not show any cross-reaction, while the peptides hPTH-(53-84) and hPTH-(1-84) produce 100% cross-reaction in the hPTH-(44-68)-RIA.

Pool I contained the total immunoreactivity measured in the hPTH-(44-68)-RIA, whereas no immunoreactivity was detectable in the other fractions.

Pool I also contained the highest C-terminal immunoreactivity, measured in the hPTH-(53-84)-RIA (company Immundiagnostik, Darmstadt, Germany). The hPTH-(53-84)-RIA, according to the data provided by the producer, has a lower limit of detection of 4 fmoles/test of the standard employed [hPTH-(53-84)]. The Intra-Assay and Inter-Assay variation coefficients are from 8.3 to 9.8% and from 11 to 14%, respectively. The synthetic hPTH peptides hPTH-(1-34), hPTH-(28-48) and hPTH-(44-68) do not show any cross-reaction, while the peptides hPTH-(64-84) and hPTH-(1-84) produce 100% cross-reaction in the hPTH-(53-84)-RIA.

Pool I (hatched) was employed for the further isolation, because here, due to measurements in two PTH-RIA, the highest concentration of C-terminal PTH fragments occurred.

2. Preparative cation exchanger chromatography of Pool I

Figure 2:
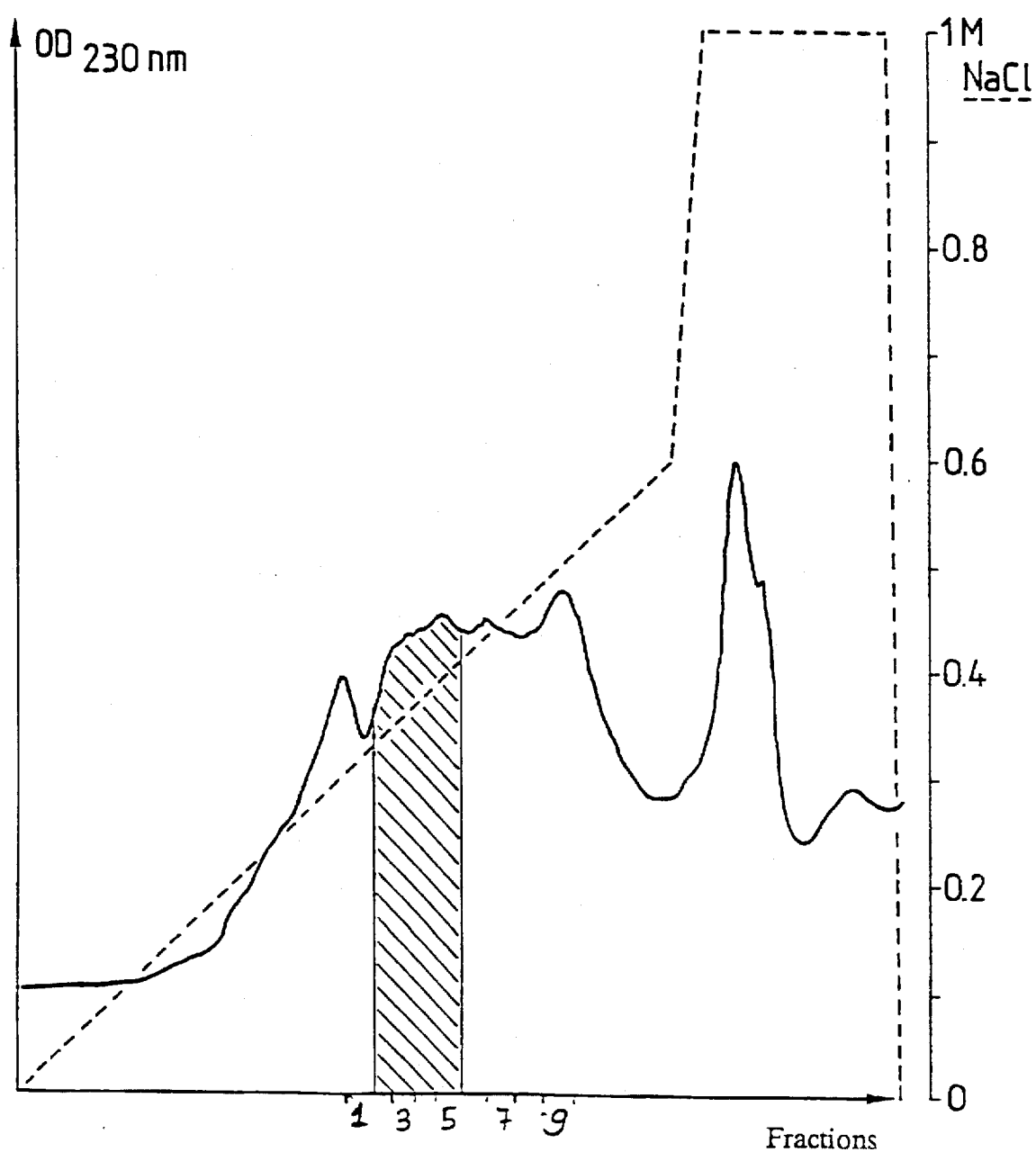
FIG. 2: Preparative HPLC cation exchanger chromatography for the further separation of the peptide material from FIG. 1. The fractions No. 2–5 of 16 ml each contain more than 640 pmoles each per fraction of hPTH-(44-68)-IR material (hatched).
Column: HPLC steel column 2 cm×10 cm
Material: Parcosil Pepkat
Eluant: A: 5 mM K2HPO4 pH 3.0; B: like A in 1M HCl
Flow Rate: 8 ml/min
Absorption: 280 nm
Gradient: 0–60% B in 60 min

A further preparative separation was effected at room temperature on a cation exchanger column (FIG. 2). A total amount of about 6 g of the material of Pool I was separated in 12 identical chromatographic runs, and the immunoreactivity of was monitored in the hPTH-(44-68)-RIA (FIG. 2). The fractions Nos. 2–5 (hatched) not shown in the Table contained the highest immunoreactivity in the hPTH-(44-68)-RIA and were pooled for further separation. They also contained the highest immunoreactivity in the hPTH-(53-84)-RIA.

3. Semi-preparative reversed-phase chromatography of the immunoreactive Pool from the preparative cation-exchanger chromatography (step 2)

Figure 3:
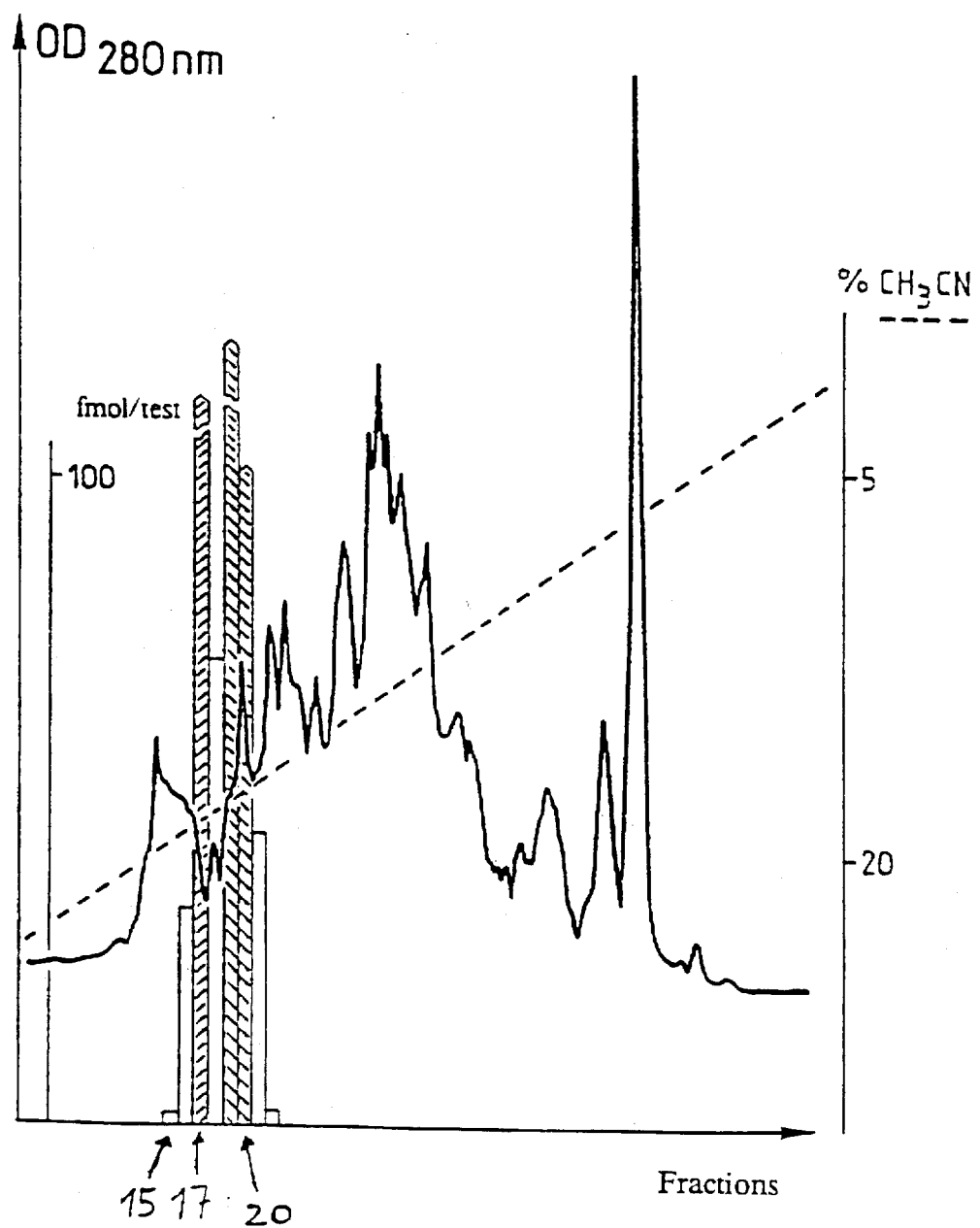
FIG. 3: Semi-preparative RP-chromatography for separating the fractions No. 2–5 of FIG. 2. In the fractions No. 17 and No. 20 of 3 ml each there are present more than 180 pmoles of hPTH fragments detectable by RIA for hPTH-(44-68).
Column: HPC steel column 1 cm×10 cm
Material: Orpegen RP HD-gel 7/300
Eluant: A: 0.01M HCl; B: like A in 80% acetonitrile
Flow Rate: 3 ml/min
Absorption: 280 nm
Gradient: 0–60% B in 60 min
Temperature: 45° C.

The immunoreactive pool (about 200 mg) was further purified over a semi-preparative reversed-phase (RP) chromatography at 45° C. (FIG. 3). The immunoreactivity in the hPTH-(53-84) -RIA ((FIG. 3) and in the hPTH-(44-68)-RIA (FIG. 3), respectively, appeared in two peaks which were incompletely separated from each other.

Figure 4:
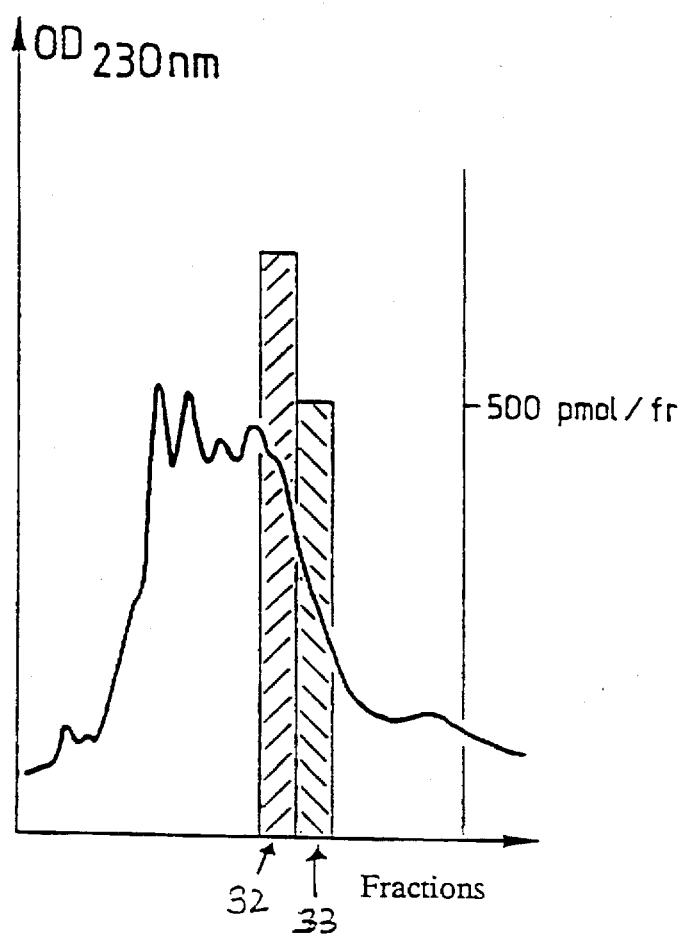
FIG. 4: Work-up of fraction 20 from FIG. 3 by means of semi-preparative cation exchanger chromatography. Fractions 32 and 33 of 10 ml each contain 750 pmoles and 600 pmoles, respectively, of a hPTH fragment which is detectable by the RIA for hPTH-(44-68).
Column: HPLC steel column 1 cm×5 cm
Material: Parcosil Pepkat
Eluant: A: 5 mM K2HPO4 pH 3.0; B: like A in 1M NaCl
Flow Rate: 3 ml/min
Absorption: 230 nm
Gradient: 0–50% B in 50 min

The workup of the rear pool which was more highly reactive in the RIA is described in greater detail hereinbelow (FIGS. 4 to 6); after passage through the steps 4 to 6 it resulted in the fraction No. 51.5 which was subjected to sequence analysis.

The fractions without designations did not contain any measurable immunoreactivity.

4. a) Semi-preparative cation-exchanger chromatography of the immunoreactive pool from the semi-preparative RP-chromatography (step 3)

The rear immunoreactive pool from the preceding RP chromatography was chromatographed on a semi-preparative cation exchanger column at room temperature (FIG. 4), and the medium-regional and C-terminal PTH-immunoreactivity (no Figure) appeared in the fractions 32–33. These were pooled (hatched area) and further processed. The fractions without designations did not contain any measurable immunoreactivity.

b) Analytical RP-chromatography of the immunoreactive pool from 4a)

Figure 5:
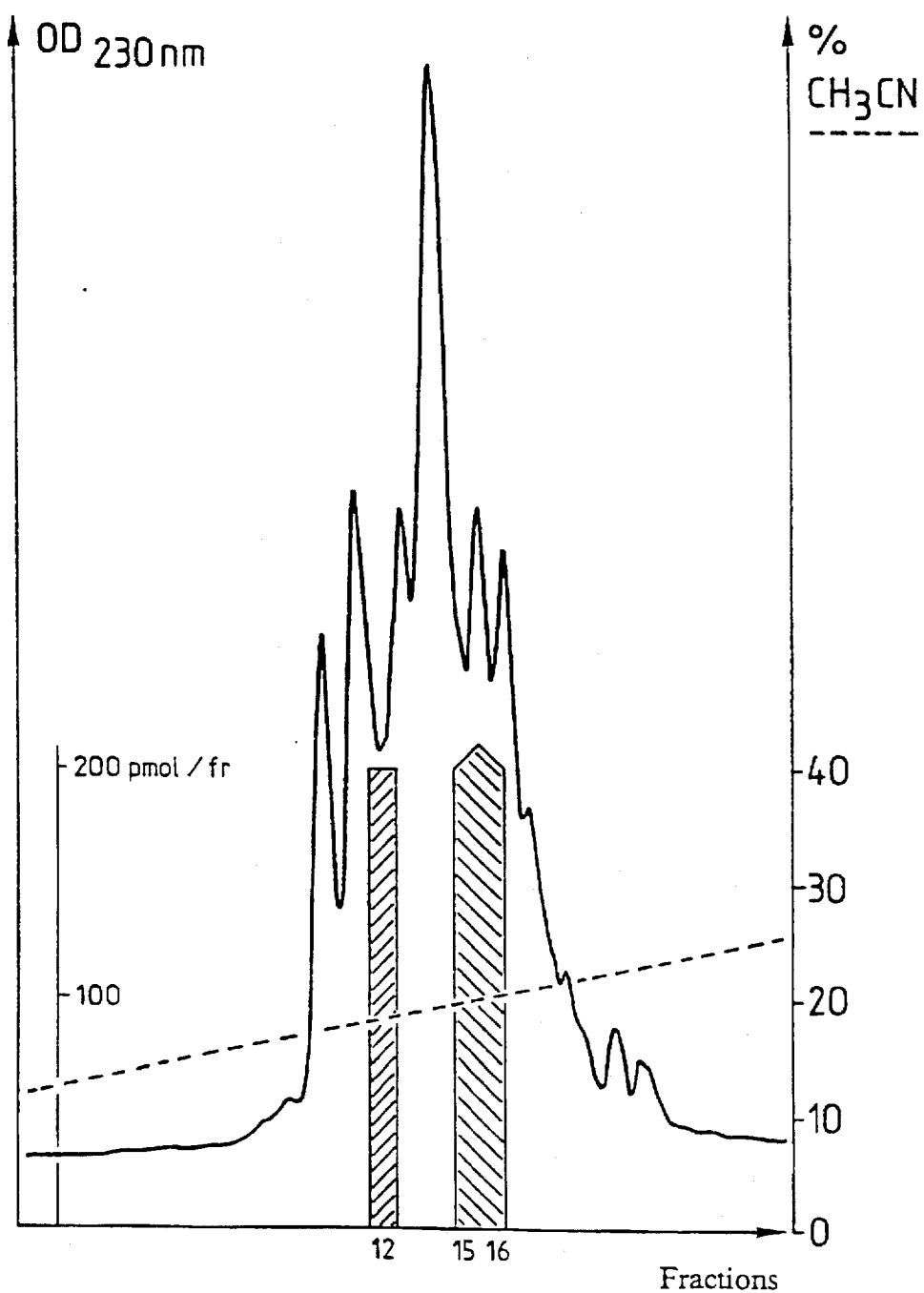
FIG. 5: Intermediate Step 1: Analytical RP chromatography of the fractions 32 and 33 of FIG. 4. Two molecule forms of hPTH-(44-68)-IR are detectable, namely in fraction 12 of 3 ml an amount in excess of 150 pmoles and in the fractions 15 and 16 of 3 ml amounts in excess of 300 pmoles in each.
Column: HPC steel column 1 cm×10 cm
Material: Orpegen RP HD-gel 7/300
Eluant: A: 0.1% TFA; B: like A in 80% acetonitrile
Flow Rate: 3 ml/min
Absorption: 280 nm
Gradient: 0–40% B in 60 min
Temperature: 45° C.

The immunoreactive pool obtained in the preceding step of semi-preparative cation-exchanger chromatography was separated on an analytical RP column at 45° C. (FIG. 5). The rear immunoreactive pool showing higher immunoreactivity (hatched) was further processed. The fractions without designations did not contain any measurable immunoreactivity.

c) Analytical cation-exchanger chromatography of the immunoreactive pool from 4b)

Figure 6:
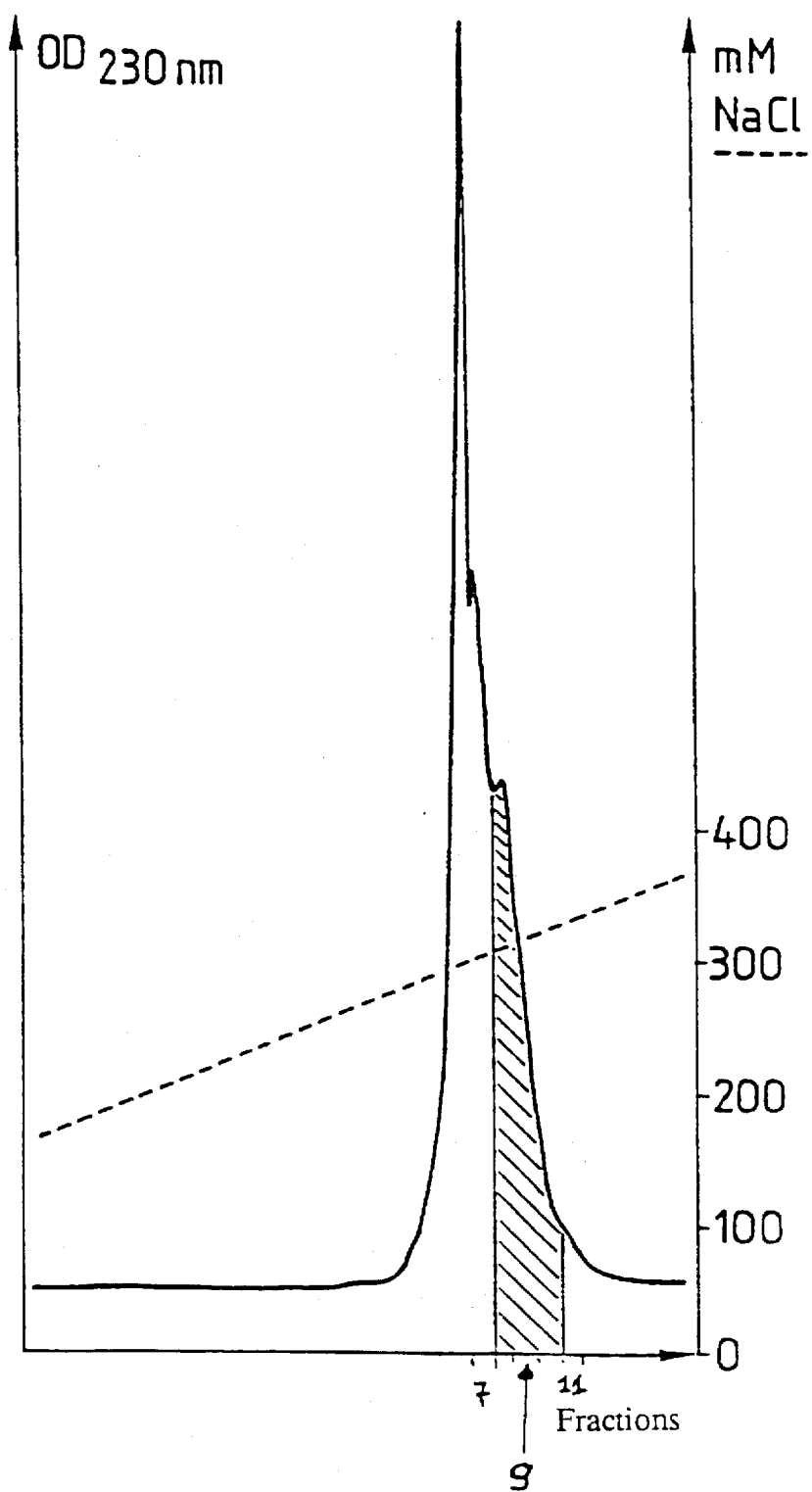
FIG. 6: Intermediate step 2: Analytical cation exchanger chromatography of the fractions 15 and 16 of FIG. 5. The hPTH-(44-68)-IR substance is particularly concentrated in fraction 9 of 2 ml (in excess of 200 pmoles).
Column: HPLC steel column 0.5 cm×5 cm
Material: Parcosil Pepkat
Eluant: A: 5 mM K2HPO4 pH 3.0; B: like A in 1M NaCl
Flow Rate: 0.7 ml/min
Absorption: 230 nm
Gradient: 0–50% B in 50 min

The immunoreactive pool was chromatographed on an analytical cation-exchanger column at room temperature (FIG. 6). The immunoreactivity in the hPTH-(44-68)-RIA is seen in FIG. 6 (hatched); the measurement in the hPTH-(53-84)-RIA resulted in the same picture. The fractions without designations did not contain any measurable immunoreactivity. The fractions exhibiting the highest immunoreactivity were pooled (hatched area) and further processed.

5. Hydrophobic interaction chromatography of the immunoreactive pool from 4c)

Figure 7:
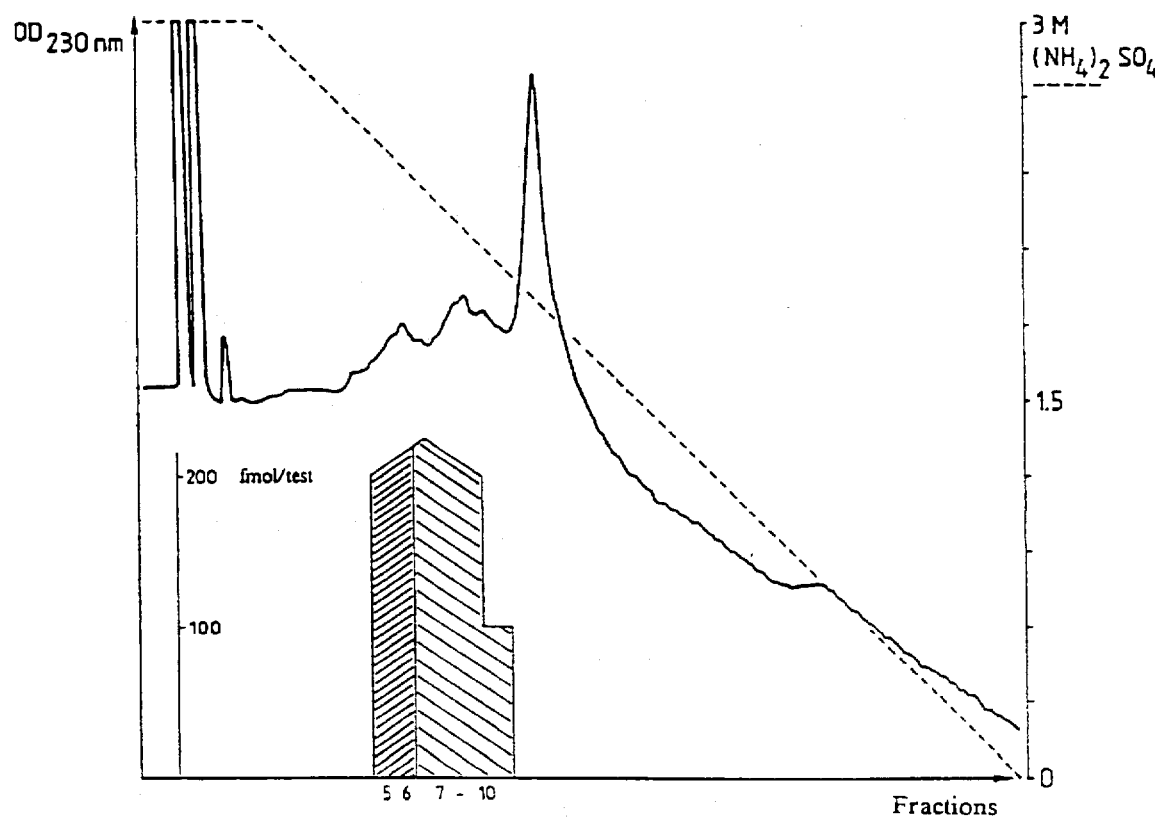
FIG. 7: Hydrophobic interaction chromatography of the fractions 8 and 9 of FIG. 6. The fractions Nos. 5–10 of 0.87 ml each contain the hPTH-(44-68)-IR material in concentrations of more than 170 pmoles/fraction.
Column: HPLC steel column 0.5 cm×5 cm
Material: Parcosil Pro HIC
Eluant: A: 100 mM Na2HPO4 pH 6.5;
B: like A in 3M (NH4)2SO4
Flow Rate: 0.7 ml/min
Absorption: 230 nm
Gradient: 100–0% B in 45 min

The immunoreactive pool from 4c) was further separated by means of the hydrophobic interaction chromatography at room temperature (FIG. 7), and the immunoreactivity was measured in the hPTH-(44-68)-RIA (FIG. 7). The fractions without designations did not contain any measurable immunoreactivity. The fractions exhibiting the highest immunoreactivity were pooled (hatched area) and subjected to the final purification.

6. a) First analytical RP chromatography

Figure 8:
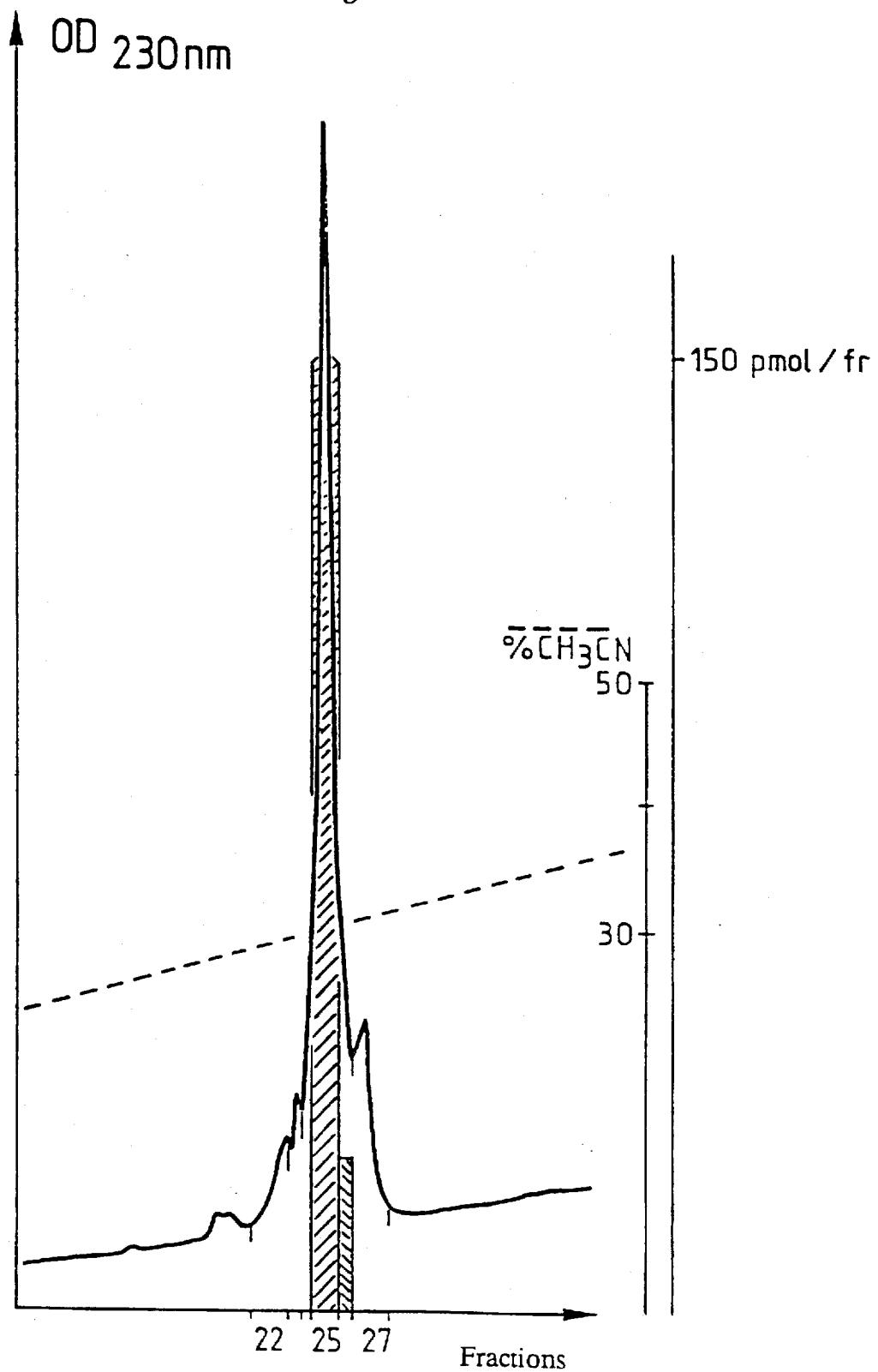
FIG. 8: Analytical RP chromatography of the fractions 5 to 10 of FIG. 7. The main peak is observed with the hPTH-(44-68)-IR.
Column: HPLC steel column 0.5 cm×5 cm
Material: Orpegen RP HD-gel 7/300
Eluant: A: 0.1% TFA; B: like A in 80% acetonitrile
Flow Rate: 0.7 ml/min
Absorption: 230 nm
Gradient: 0–40% B in 60 min
Temperature: 45° C.

The immunoreactive pool from 5) was chromatographed on an RP column at 25° C. and the immunoreactivity was monitored by means of the hPTH-(44-68)-RIA (FIG. 8). The fractions shown by the hatched areas were re-chromatographed.

b) Second analytical RP chromatography

Figure 9:
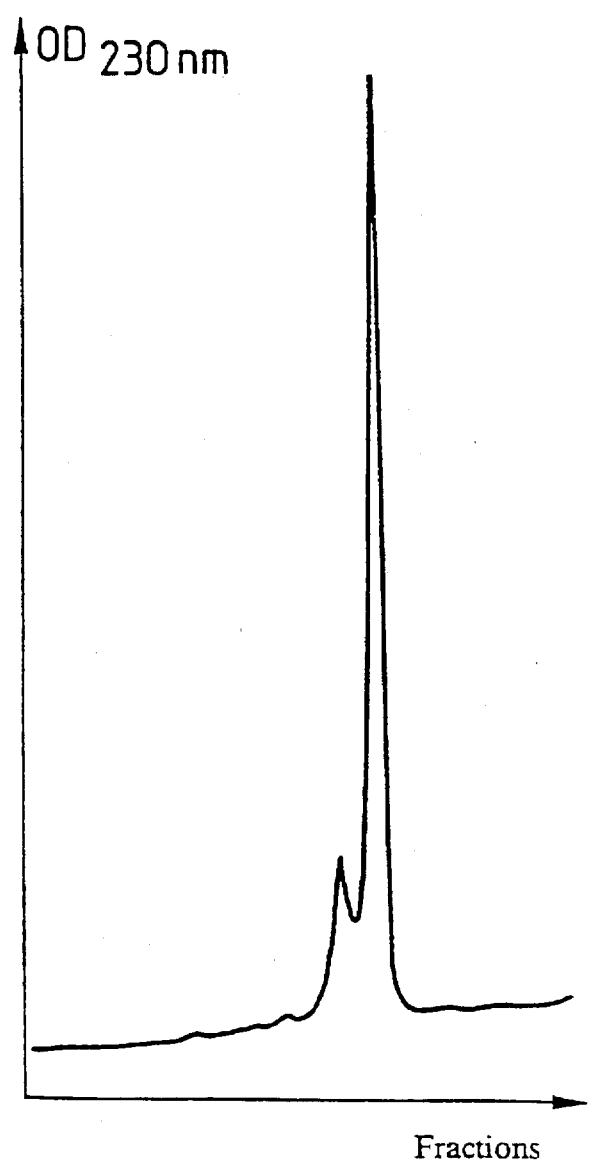
FIG. 9: Analytical RP chromatography for the final purification of the hPTH fragment. The material of fraction 25 from FIG. 8 was re-chromatographed, and in the main peak there results a highly pure peptide, the sequence of which was determined to be hPTH-(38-84).
Column: HPLC steel column 0.5 cm×5 cm
Material: Orpegen RP HD-gel 7/300
Eluant: A: 0.1% TFA; B: like A in 80% acetonitrile
Flow Rate: 0.7 ml/min
Absorption: 230 nm
Gradient: 0–40% B in 60 min
Temperature: 45° C.

The immunoreactive pool from 6a) was once more passed through an RP column (FIG. 9). Except for the temperature which in this chromatography was 45° C. the conditions were the same as in step 6a). The material of the higher peak designated by the Code No. 51.5 was sequenced.

III. Isolation of a second fraction (Code No. 54.5) exhibiting immunoreactivity in medium-regional- and C-terminal-specific radioimmunoassays for parathormone (PTH)

During the isolation of the fraction 51.5, in the semi-preparative RP chromatography (step 3) there were obtained two pools exhibiting immunoreactivity. The work-up of the front pool of step 3 was carried out in a manner identical with that described for the rear pool in II. 4 to 6. In step 4b) again there were seen two immunoreactive peaks; in this case the front peak was predominant and was further processed. After passing the steps 4c) through 6c), a fraction designated by the Code No. 54.5 was obtained, which was also subjected to sequence analysis.

IV. Sequencing the PTH peptides isolated from hemofiltrate and exhibiting immunoreactivity in medium- regional- and C-terminal-specific radioimmunoassays for parathormone (PTH)

The fractions 51.5 and 54.5, the isolation of which from hemofiltrate has been described in II and III, were sequenced by means of the Gas Phase Sequenator Type 470 A (Applied Biosystems). The EDMAN degradation (Edman and Begg, Eur. J. Biochem. 1, 80–91, 1967) was carried out using the standard program PTHRUN. The analysis of the derivatized amino acids was performed by the on-line method using an ABI 120 A chromatograph employing the standard protocol ABI For the fraction 51.5 a sequence of 39 amino acids could be determined; 5 more amino acid moieties could be determined only with reservation. The sequence found conforms to the section (38–76) of human pTH (Keutmann et al., Biochem. 17, 5723–5729, 1978).

For the fraction 54.5 a sequence of 16 amino acids could be determined. The sequence found conforms to human PTH-(38-53).

Two fractions could be isolated from human hemofiltrate, both of which were detected in a medium-regional as well as in a C-terminal PTH-RIA. Both peptides begin with the amino-terminal sequence Gly-Ala-Pro-Leu-Ala-Pro-Arg-etc., the amino acid 38 of the hPTH molecule. For both of the peptides found the last C-terminal amino acid cannot be indicated with certainty. In the case of the fraction 51.5, sequencing could be continued almost to the position 84. The other peptide, of which only 16 positions could be determined by sequence analysis because of the smaller quantity available, has a sequence length of at least 30 amino acids, because otherwise it would not be detected in the C-terminal RIA. C-terminal PTH peptides having a different N-terminal beginning of the sequence could not be isolated. These results allow the conclusion to be drawn that the hPTH-(1-84) is cleaved between the amino acids 37 and 38 and that thereupon the biologically active fragment hPTH-(1-37) is formed.

EXAMPLE 2

Synthesis of Human Parathormone Peptide hPTH-(1-37)

1. Synthesis of the kieselguhr-reinforced Fmoc-Leu-resin

The Fmoc-amino acid anhydride (5 equivalents) was dissolved in a minimum volume of N,N-dimethylformamide (DMF) and was added to the hydroxymethylphenoxyacetyl-norleucin resin in a round-bottom flask. 4-Dimethylaminopyridine (1 equivalent) was also dissolved in a minimum volume of DMF and added into the round-bottom flask. After one hour of reaction time the excess of the reagents was removed by filtration, and the resin was thoroughly washed on a filter.

2. Strategy of the synthesis of the human parathormone peptide hPTH-(1-37)

For the synthesis of the peptide having the formula

Ser-Val-Ser-Glu-Ile-Gln-Leu-Met-His-Asn-Leu-Gly-Lys-His-Leu-Asn-
Ser-Met-Glu-Arg-Val-Glu-Trp-Leu-Arg-Lys-Lys-Leu-Gln-Asp-Val-His-
Asn-Phe-Val-Ala-Leu (SEQ ID NO: 1)

the flow method (Atherton and Sheppard, Solid phase peptide synthesis. IRL Press, Oxford 1989) was employed. The above-defined peptide sequence was synthesized by means of an automatic peptide synthesis apparatus (Milligen 9050) using the Fmoc-pentafluorophenyl esters (OPfp). The following Fmoc-amino acid OPfp's were used in an excess (4 equivalents) (in each case the derivatives of the L-amino acids were employed).

| | |
|---|---|
| Fmoc-Ala-OPfp | Fmoc-Ala |
| Fmoc-Asp(OBut)-OPfp | Fmoc-Asp(OBut) |
| Fmoc-Met-OPfp | Fmoc-Met |
| Fmoc-Glu(OBut)-OPfp | Fmoc-Glu(OBut) |
| Fmoc-His(Trt)-OPfp | Fmoc-His(Trt) |
| Fmoc-Leu-OPfp | Fmoc-Leu |
| Fmoc-Arg(Mtr)-OPfp | Fmoc-Arg(Mtr) |
| Fmoc-Trp-OPfp | Fmoc-Trp |
| Fmoc-Lys(BOC)-OPfp | Fmoc-Lys(BOC) |
| Fmoc-Ile-OPfp | Fmoc-Ile |
| Fmoc-Phe-OPfp | Fmoc-Phe |
| Fmoc-Gly-OPfp | Fmoc-Gly |
| Fmoc-Asn-OPfp | Fmoc-Asn(Trt) |
| Fmoc-Gln-OPfp | Fmoc-Gln(Trt) |
| Fmoc-Val-OPfp | Fmoc-Val |
| Fmoc-Ser(But)-ODhbt | Fmoc-Ser(But) |

The synthesis can also be carried out by means of hydroxybenzotriazole esters formed in situ by the addition of TBTP [O-(1H-benzotriazol-1-yl)-N,N,N',N'-tetramethyl uronium tetrafluoroborate].

The peptide was removed from the carrier resin by addition of a mixture of trifluoro acetic acid-anisole-ethanedithiol-phenol 94:2:2:2 (v/v/v/w) and precipitated with ether. The HPLC-purified peptide was characterized by amino acid analysis, analytical HPLC and amino acid sequence analysis.

3. Practical realization of the synthesis of the humane parathormone peptide hPTH-(1-37)
The synthesis of Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Val-Ala-Leu (I) hPTH-(1-37) (SEQ ID NO: 1)

was carried out according to the continuous flow-method using the automatic 9050 PepSynthesizer (Program Version 1.3) MilliGen/Biosearch. Fmoc-amino acid penta fluorophenyl esters were used in the L-configurations and in portions of 0.8 mmoles each. All reagents necessary for the synthesis were supplied from Milligen/Biosearch: N,N-dimethylformamide, 20% piperidine in N,N-dimethylformamide and 1-hydroxy benzotriazole. The L-amino acid derivatives were employed in a fourfold excess. The terminal amino groups were Fmoc-protected. Aspartic acid and glutamic acid were employed as $N^W$-tert-butyl esters; tyrosine and serine were employed as tert-butyl ethers; histidine and lysine were employed as $N^W$-Boc compounds, and Arg was employed as $N^G$-2,2,5,7,8-pentamethylchromane-6-sulfonyl(Pmc) derivative. The synthesis was carried out starting from the kieselguhr resin Fmoc-Leu-Pepsyn KA (MilliGen/Biosearch), that is with carrier-bonded C-terminal amino acid (0.091 meq of leucine per gram, 1.60 g). The acylation of Fmoc-Arg(Pmc)-OH was carried out in the presence of [O-(1H-benzotriazol-1-yl)-N,N,N',N'-tetramethyluronium tetra fluoroborate] (TBTU), 1-hydroxybenzotriazole and diisopropylethylamine. The following synthesis cycle was employed. Fmoc-removal with 20% of piperidine in DMF (7 min), washing with DMF (12 min), acylation (30 min; for Fmoc-ValOPfp 45 min), and washing with DMF (8 min). The progress of the synthesis was monitored by continuous UV detection. The synthesis was terminated with the removal of the N-terminal Fmoc-group. The resin-bonded peptide was washed three times with 50 ml each of isopropanol, glacial acetic acid, isopropanol and diethylether and dried.

The removal from the carrier resin was effected with trifluoroacetic acid/phenol/ethanedithiol/thioanisole/water 10:0.75:0.25:0.5:0.5 (v/w/v/v/v; 5 ml). The solution is concentrated in vacuo, and the product is precipitated by the addition of diethylether. The resulting crude peptide is washed several times with diethylether and dried. Thus, 65 mg of crude peptide are obtained from 240 mg of peptide resin.

Figure 16:
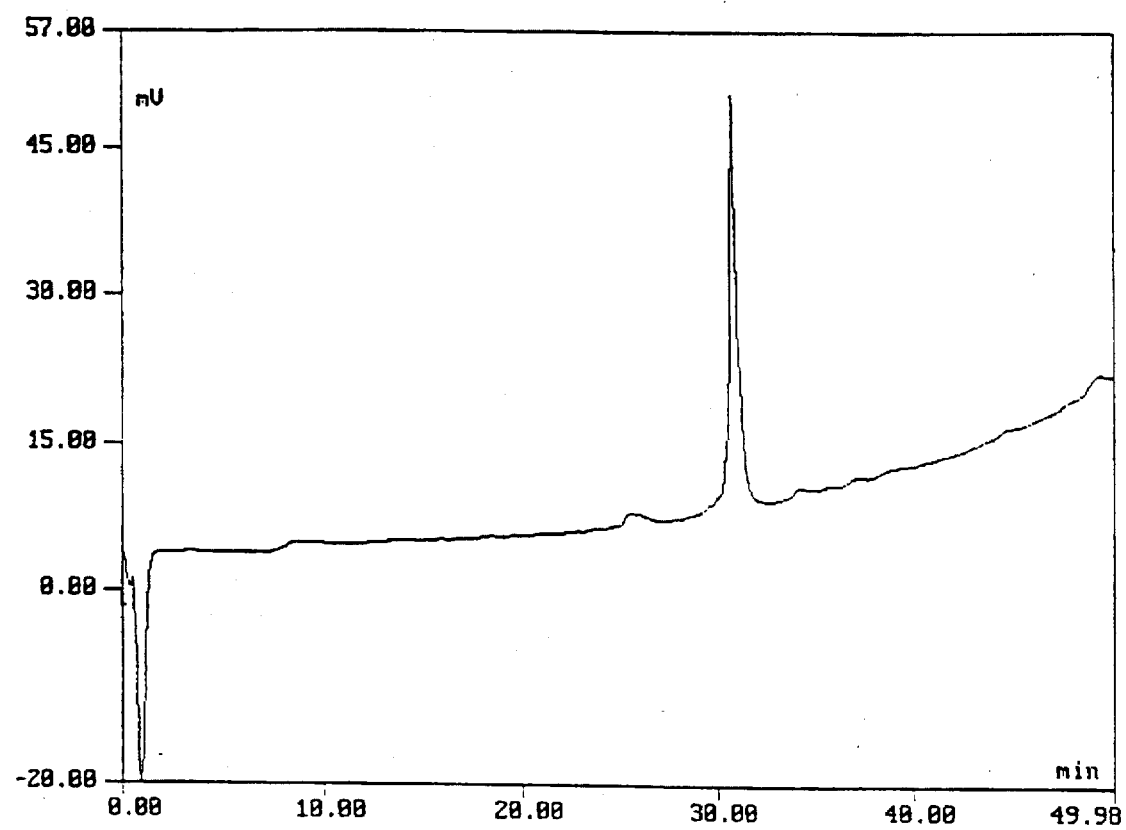
Figure 17:
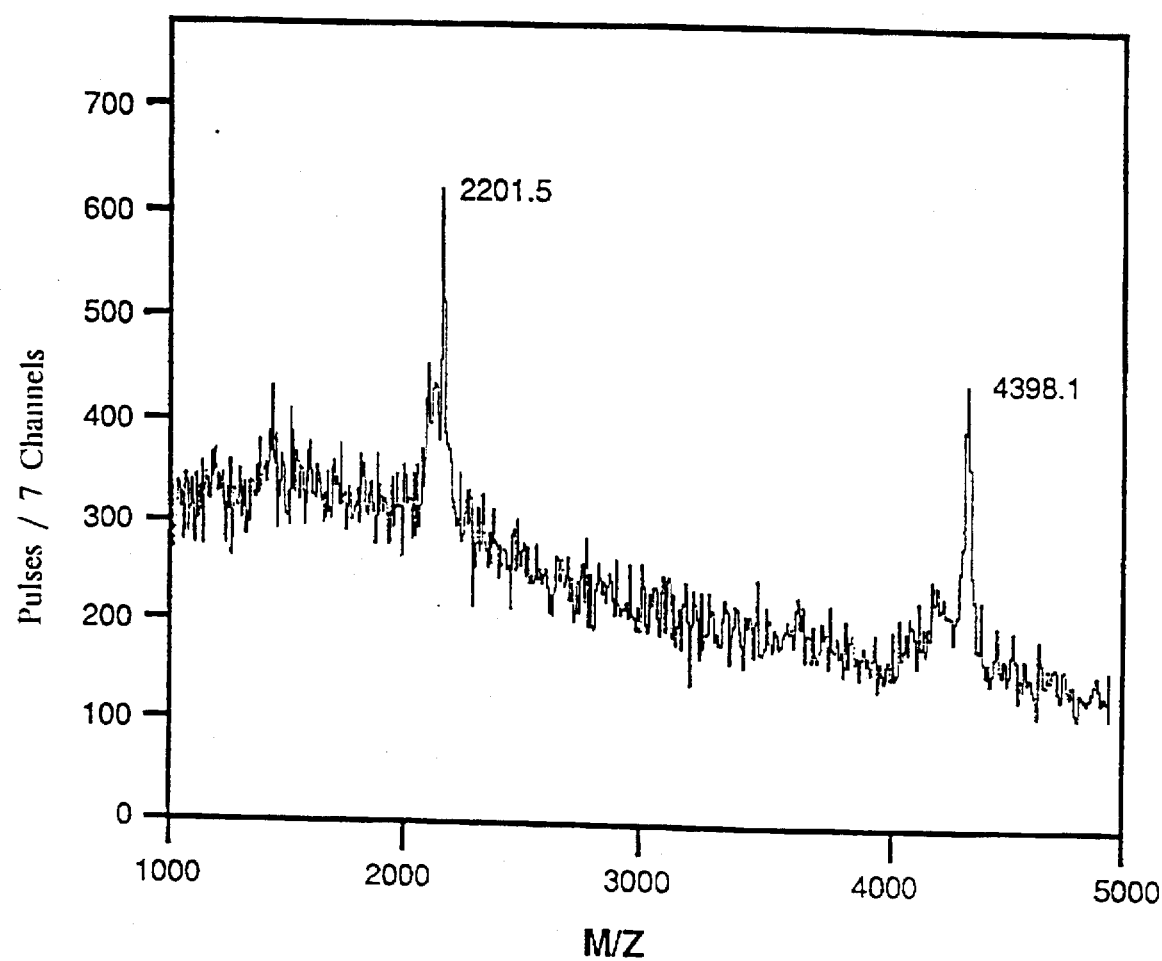

The purification was carried out using a standard of hPTH-(1-37) prepared in an independent synthesis, the correct sequence of which had been confirmed by MS (mass spectrometry) and sequence analysis. In the first step, the de-blocked crude material was purified by cation-exchanger HPLC (Parcosil PepKat, 2 cm×10 cm, 300 Å, 7 μ, flow rate 9 ml/min, 230 nm, eluant A=5 mM $NaH_2PO_4$; B=5 mM $NaH_2PO_4$+1M NaCl, gradient: 5% 100% in 60 minutes), the main peak appearing at 28.17 min (FIG. 14) in concordance with the reference substance. In the second purification step, with simultaneous RP-HPLC for de-salting (Parcosil ProRP C4, 2 cm×10 cm, 300 Å, 7 μ, flow rate 7 ml/min, 230 nm, eluant A=0.1% trifluoroacetic acid in water; B=0.1% trifluoroacetic acid in acetonitrile/water 4:1, gradient 0% 100% B in 60 minutes), yield: 6.6 mg (1.5 mmoles; 14.8%), there was obtained a peak at 30.80 min (FIG. 15) which, in an analytical RP-HPLC using C18 material gives a sharp uniform peak (FIG. 16).

The identity of the synthesized material with the given primary structure of PTH-(1-37) was proven by MS (plasma desorption method, Bio-Ion, Applied Biosystems) (FIG. 17) and counter-sequencing in a Gas Phase Sequenator (Model 470, Applied Biosystems). The biological activity of the synthetic PTH-(1-37) was furnished evidence of in the function test by differential muscle contraction of pulmonal arteries over Arteria renalis: The test showed that the synthetic material has the correct biological activity.

EXAMPLE 3

Evidence of the Biologically Active Circulating Human PTH as hPTH-(1-37)

Figure 10:
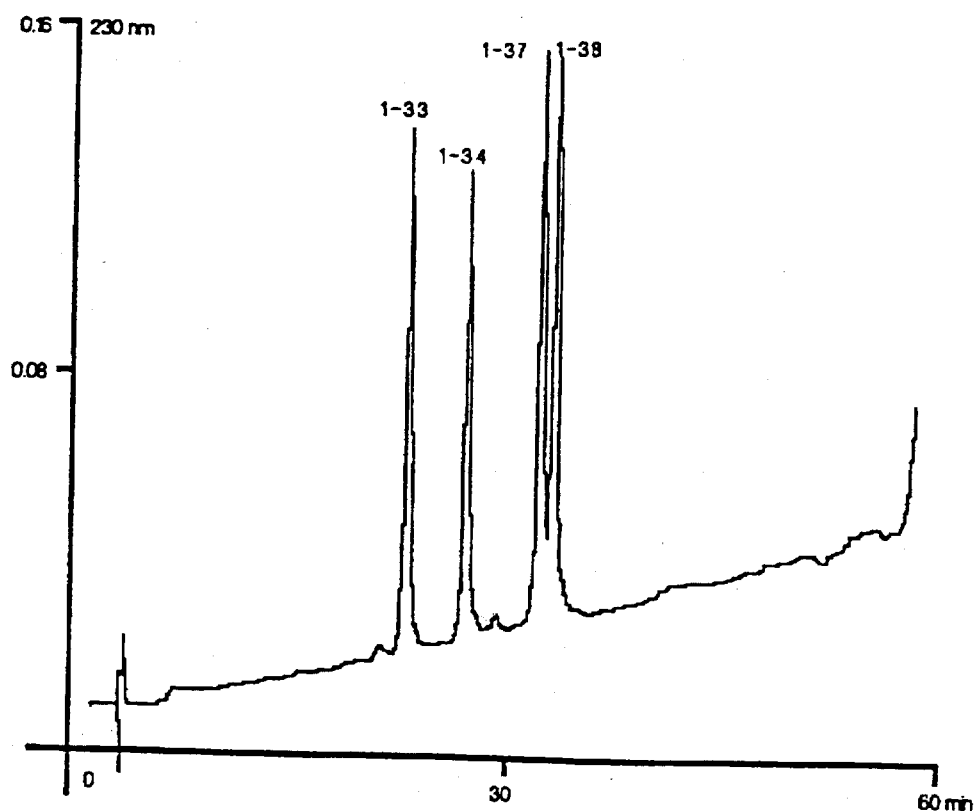
FIG. 10: Reversed-phase HPLC chromatography of the synthetic hPTH fragments from the N-terminal range, namely hPTH-(1-33), hPTH-(1-34), hPTH-(1-37), hPTH-(1-38). If these fragments are used as reference for natural fragments of the N-terminus of hPTH circulating in blood, then it can be shown that the hPTH-(1-37) is the correct molecule form in the human blood.
Column: Parcosil ProRP 300-7, C4, 125×4 mm
Temperature: 55° C.
Eluant: A: 0.1% trifluoroacetic acid
B: like A+80% acetontrile
Gradient: Start:—25% B 55 min—50% B 60 min—100% B
Absorption: 230 nm
Flow Rate: 0.7 ml/min

As described in Example 1, the hemofiltrate was worked-up by chromatographic procedures, the synthetic hPTH-(1-37) according to Example 2 being utilized as the reference substance (FIG. 10). Thus, from the hemofiltrate a fraction could be demonstrated which exhibited immunoreactivity of amino-regional specificity in the hPTA-radioimmunoassay. This fraction was purified in the same manner as in Example 1 and characterized as hPTH-(1-37). Evidence was furnished of that by means of the Parcosil-RP column employed the hPTH-(1-37) can be unambiguously distinguished from further PTH fragments (FIG. 10), namely hPTH-(1-33), hPTH-(1-34), and hPTH-(1-38).

EXAMPLE 4

Functional Analysis of hPTH-(1-37) for Furnishing Evidence of its Biological Activity Change of the intracellular level of cyclic 3',5'-adenosine monophosphate (cAMP) in pheochromocytoma cells (PC-12) of the rat after application of humane parat-hormone peptides hPTH-(1-33), hPTH-(1-37) and hPTH-(1-38).

In preliminary experiments it was shown that a pheochromocytoma line of the rat (PC-12) responds to an addition of PTH by increasing the intracellular CAMP level. Thereupon, the activity of the synthetic hPTH-(1-37) peptide was compared to the activities of other N-terminal PTH fragments [hPTH-(1-33) and hPTH-(1-38)] in this cell system.

A PC-12 cell line was used. The cells were cultured in RPMI medium 1640 (Gibco) with 10 ml/l of L-glutamine 200M (Gibco), 10% of equine serum, 5% of FCS, and 1% of penicillin/streptomycin. As the phosphodiesterase inhibitor there was used 4-isobutyl-1-methylxanthine (IBMX) from Sigma. Culture dishes comprising 24 wells (16 mm in diameter) (Costar) coated with poly-L-lysine were used. Coating was effected by applying a sterile-filtered poly-L-lysine solution (100 mg/l) at 37° C. for one hour.

The following hPTH peptides were investigated:

hPTH-(1-33) (MW 3971.2; peptide content 76.9%); hPTH-(1-37)(MW 4401.0; peptide content 74.5%); and hPTH-(1-38) (MW 4458.0; peptide content 81.8%).

Figure 11:
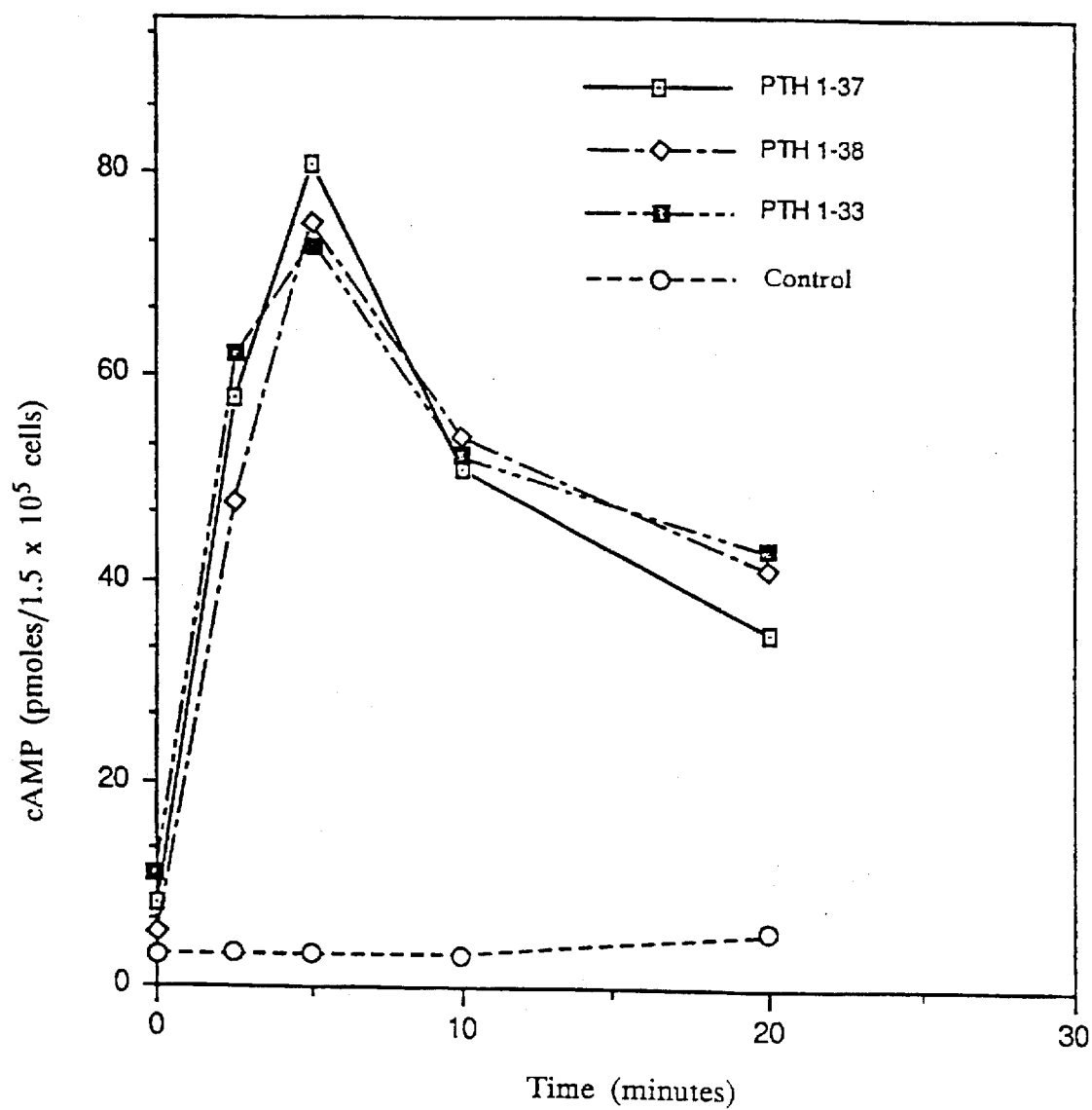
FIG. 11: Time dependence of the intracellular cAMP concentration of PC-12 cells after the stimulation with hPTH fragments. 1.5×105 cells were incubated with $10^{-7}M$ hPTH-(1-33), hPTH-(1-37), and hPTH-(1-38) in the presence of $10^{-4}M$ IBMX for 0, 2.5, 10 and 20 minutes. For control, the cells were incubated with only IBMX for 20 minutes. The values are average results of triple experiments S.D.

The cells were used after the formation of a dense cell sheet (after about 4–8 days). The incubation was carried out with 1 ml of cell medium at room temperature. The PTH peptides were diluted with cell medium immediately before the beginning of the assay. In the first run of the assay, $1.5 \times 10^5$ cells were incubated with $10^{-7}$M of hPTH-(1-33), hPTH-(1-37) and hPTH-(1-38) in the presence of $10^{-4}$M IBMX for 0, 2.5, 5, 10 and 20 minutes. For control, cells were incubated with only IBMX for 20 minutes. The values are average values from triple runs±S.D. (cf. FIG. 11).

Figure 12:
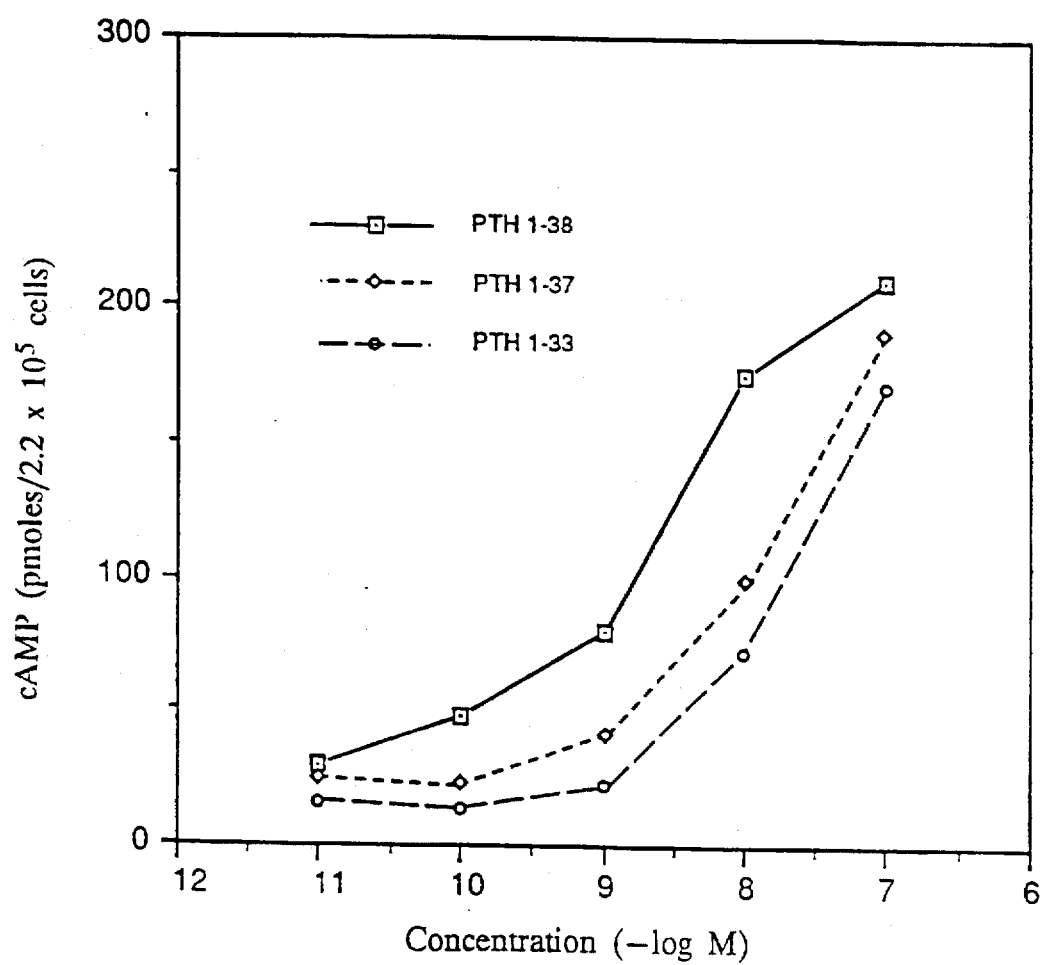
FIG. 12: Dose-effect relation between the concentrations of hPTH-(1-33), hPTH-(1-37), and hPTH-(1-38) and the intracellular cAMP level in PC-12 cells after 5 minutes of stimulation. 2.2×105 PC-12 cells were incubated each with $10^{-11}$ (double run), $10^{-10}$, $10^{-9}$, $10^{-8}$ and $10^{-7}M$ of each of hPTH-(1-33), hPTH-(1-37), and hPTH-(1-38) in triple experiments in the presence of $10^{-4}M$ IBMX for 5 minutes, and the intracellular cAMP concentration was measured.

In a second experimental run, $2.2 \times 10^5$ PC-12 cells were incubated each with $10^{-11}$ (double run), $10^{-10}$, $10^{-9}$, $10^{-8}$ and $10^{-7}$M of each of hPTH- (1-33), hPTH-(1-37), and hPTH-(1-38) in triple experiments in the presence of $10^{-4}$M IBMX for 5 minutes, and the intracellular cAMP concentration was measured. The IBMX control values without PTH were 18.0, 26.1, 20.9. The values depicted are average values S.D. (cf. FIG. 12).

Both PTH and IBMX were added at the same time. After suction-removal of the medium the reaction was stopped by the addition of 1 ml of 99% ethanol. The cells were scraped off and were transferred into plastics tubes (Greiner) with the ethanol. The culture dish was rinsed with 66% ethanol, the supernatants were combined and centrifuged. The supernatant was evaporated on the water bath (50° C.) while purged with nitrogen gas. The concentration of the cAMP was determined using a radioimmunoassay kit (NEN). The measurement was carried out in accordance with the producer's instructions. The amounts employed of cAMP standard, cAMP anti-serum complex, cAMP $^{125}$I-tracer concentrate, cAMP carrier serum and cAMP precipitator were 50% of the amounts indicated by the producer.

The results show that significant differences exist in the activity of hPTH-(1-37) in comparison to the activities of other, non-endogenous PTH peptides in the cell system investigated. This result allows to conclude differences in the conformations of these peptides which, as has been shown here, affect the activation of the PTH receptor-adenylate cyclase system, but, moreover, also affect the antigenicity.

EXAMPLE 5

Investigations Relating to the Secondary Structure of the Parathormone Fragments hPTH-(1-33), hPTH-(1-37) and hPTH-(1-37) by Circular Dichroism The circular dichroism was measured by means of a Jasco J-500 Automatic Recording Spectropolarimeter coupled with a Jasco DP-500 Data Processor. For the determination of the secondary structure, the measurement was carried out in the spectral range of from 190 nm to 240 nm at room temperature in a selected quartz cuvette at a light path of 1 mm. The parathormone concentrations employed were 50 µg/ml of hPTH-(1-33), 50 µg/ml of hPTH-(1-37) and 50 µg/ml of hPTH-(1-38). 10 mM Tris-HCl buffer pH 7.5 was used for dissolution (other conditions of the measurement: Sensitivity 2 milli-degrees/cm; time constant 2 seconds; recorder speed: 4 nm/min; wave length expansion: 5 nm/cm). The curves in FIG. 13 for hPTH-(1-33) hPTH-(1-37) and hPTH-(1-38) are average values for the signals from 4 subsequent measurements minus the base line values.

The evaluation for determining the secondary structure was performed in accordance with the method described by Reed and Kinzel (Biochemistry 23, 1357–1362, 1984).

From the data available, for the secondary structure of hPTH-(1-38) an -helix proportion of about 27% was calculated. The PTH fragment shorter by one amino acid [hPTH-(1-37)], in contrast thereto, has a significantly higher proportion of the α-helix structure of about 40–45%. The amount of -helix in the hPTH-(1-33) in turn is similarly low as in hPTH-(1-38).

From the investigation it follows that, due to the significant differences in the secondary structures, the peptide-receptor interactions and immuno-epitope properties of the PTH fragment hPTH-(1-37) must be clearly different from those of the other fragments.

EXAMPLE 6

Investigations Relating to the Biological Activity of hPTH-(1-37) on the Unstriated Muscles of the Pulmonary Vessels and of the *Corpus cavernosum* (Male Genital Organ)

The unstriated muscles of the lung vessels and of the *Corpus cavernosum* were recovered from human surgical preparations and from rabbits and were fixed in a suitable organ bath system to measure the development of force. It was determined that these muscles, in comparison to other smooth muscles of the human organism, after pre-contraction with various contraction-activating substances, exhibit a distinct relaxation after the addition of hPTH-(1-37) in concentrations in the range of $10^{-9}$ moles, which furnishes evidence of the fact that the hPTH-(1-37) is a particularly suitable peptide for the vasorelaxation of the pulmonary vessels and the activation of blood circulation of the male member.

---

We claim:

1. An isolated hPTH fragment-(1-37) consisting of the amino acid sequence according to SEQ ID NO:1 or an amidated, acetylated, phosphorylated, or glycosylated derivative thereof.

2. A method for treating hypoparathyroidism comprising administering to a patient in need of such treatment, an amount of the fragment according to claim 1 effective to treat hypoparathyroidism.

3. A process for the preparation of an hPTH-fragment-(1-37) which has the amino acid sequence according to SEQ ID NO:1, comprising the steps of (a) expressing a nucleic acid encoding the fragment in a prokaryotic or eukaryotic organism and (b) purifying the fragment expressed by a chromatographic procedure.

4. A process for the preparation of an hPTH fragment-(1-37) comprising isolating the fragment from human blood by chromatography, wherein said hPTH fragment-(1-37) has the amino acid sequence according to SEQ ID NO:1.

5. A pharmaceutical preparation comprising a therapeutically effective amount of the hPTH fragment-(1-37) of SEQ ID NO:1 in combination with a pharmaceutically acceptable carrier.

6. The pharmaceutical preparation according to claim 5, wherein said fragment is in lyophilized form and is combined with mannitol.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 37 amino acids
( B ) TYPE: amino acid
( D ) TOPOLOGY: linear (i i) MOLECULE TYPE: peptide (i i i) HYPOTHETICAL: YES (v) FRAGMENT TYPE: N-terminal (v i) ORIGINAL SOURCE:
  (A) ORGANISM: Human (x i) SEQUENCE DESCRIPTION: SEQ ID NO:1:

```
Ser Val Ser Glu Ile Gln Leu Met His Asn Leu Gly Lys His Leu Asn
 1           5                   10                      15
Ser Met Glu Arg Val Glu Trp Leu Arg Lys Lys Leu Gln Asp Val His
            20                  25                  30
Asn Phe Val Ala Leu
            35
```